United States Patent [19]
Herskovitz et al.

[11] 3,954,821
[45] May 4, 1976

[54] CARBON DIOXIDE COMPLEXES OF RH, IR, NI, PD, AND PT

[75] Inventors: Thomas Herskovitz; George William Parshall, both of Wilmington, Del.

[73] Assignee: E. I. Du Pont de Nemours and Company, Wilmington, Del.

[22] Filed: June 30, 1975

[21] Appl. No.: 592,074

[52] U.S. Cl. ............... 260/429 R; 252/429 R; 252/431 R; 252/431 C; 252/431 N; 252/431 P; 260/439 R; 260/677 R; 260/677 H
[51] Int. Cl.[2] ............... C07F 15/00; C07F 15/04
[58] Field of Search ............ 260/429 R, 439 R

[56] References Cited
UNITED STATES PATENTS

| | | | |
|---|---|---|---|
| 3,452,068 | 6/1969 | Wilkinson | 260/429 R |
| 3,459,780 | 8/1969 | Wilkinson | 260/429 R |
| 3,538,133 | 11/1970 | Knoth | 260/429 R |

OTHER PUBLICATIONS

Katsuhiko et al., J. Orgmet Chem. 69 (1974), pp. 151–159.
Kolomnikov et al., J. Orgmet Chem. 67 (1947), pp. C25–C27.
Komiya et al., J. Orgmet Chem. 46 (1972), pp. C58–C60.
Iwasaita et al., J. Am. Chem. Soc. 91 (1969), pp. 2525–2528.
Jolly et al., J. Orgmet Chem. 33 (1971), pp. 109–122.
Floriani et al., Chem. Comm. 1974, pp. 615–616.
Flynn et al., Chem. Comm. 1974, pp. 703–704.
Volpin et al., Chem. Abstracts 78 (1970) No. 8798v.

*Primary Examiner*—Arthur P. Demers

[57] ABSTRACT

Complexes of certain transition metals and phosphine or arsine ligands with carbon dioxide, e.g., (carbon dioxide)bis[1,2-ethanediyl-bis[dimethylphosphine]-P,P']iridium(1+), chloride, useful as catalysts in hydrogenation and isomerization, e.g., of 1-butene, are prepared by direct addition of pressurized $CO_2$ to the appropriate metal complex precursor, e.g.,

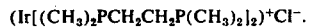

16 Claims, No Drawings

CARBON DIOXIDE COMPLEXES OF RH, IR, NI, PD, AND PT

BACKGROUND OF THE INVENTION

1. Field of the Invention

This invention is concerned with a new class of metal complexes containing carbon dioxide as a ligand.

2. Prior Art

Carbon monoxide is well known in ligand form and many metal complexes containing it have been examined. Only a very few metal complexes containing carbon dioxide as a ligand have been reported. Most of these contain two atoms of metal for each ($CO_2$) ligand.

For example, Iwashita et al., J. Am. Chem. Soc., 91, 2523-8, 1969, show $Rh_2(CO)_2(CO_2)[P(C_6H_5)_3]_3$. Vol'pin et al., Acad. Sci., USSR, Div. of Chem. Sci., Bulletin, 1969, 1945, show $(PPh_3)_3RhCl \cdot CO_2 \cdot (PPh_3)_3RhCl$. Jolly et al., J. Organometal. Chem., 33 109–122, 1971, show $Ni_2[P(C_6H_{11})_3]_4CO_2$. Floriani et al., Chem. Comm. 1974, 615–6, show $Co(N,N'$-salicylideneiminato$)CO_2 \cdot 2Na$. And Flynn et al., Chem. Comm., 1974, 703–4, show $CO_2M(OH)(CO)(Ph_3P)_2$ where M is Rh or Ir.

SUMMARY AND DETAILS OF THE INVENTION

There have now been discovered the carbon dioxide/metal complexes of formula I $$ML_m(CO_2)_nX_p \qquad \text{I}$$

in which:

M is Rh, Ir, Ni, Pd or Pt,

L is one equivalent of an acyclic tertiary alkyl phosphine or arsine ligand in which each alkyl group is saturated and may contain up to 18 carbon atoms, X is one equivalent of an anion, and when M is Rh or Ir, $m$ is 3 or 4, $n$ is 1 or 2, $p$ is 1, and $m + n$ does not exceed 5;

when

M is Ni, Pd or Pt, $m$ is 3, $n$ is 1, and $p$ is 0;

and a process for preparing them according to the equation $$ML_mX_p + nCO_2 \rightarrow ML_m(CO_2)_nX_p$$
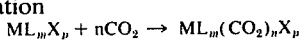

in which M, L, X, $m$, $n$, and $p$ are defined as above.

The anions embraced in the definition of X above include halogens such as fluoride, chloride, bromide and iodide, nitrate, nitrite, cyaninde, acetate, trifluoroacetate, propionate, butyrate, benzoate, oxalate, sulfide, sulfate, phosphate, hexafluorophosphate, tetraphenylborate and the like.

The process of this invention may be conducted neat, i.e., without any added agents. The carbon dioxide may be supplied in gaseous or liquid form.

It is preferable to carry out the reaction in the presence of a reaction medium which may be any liquid which is inert to the reactants and products. The reaction medium may be excess liquid $CO_2$ or an organic liquid such as a hydrocarbon (e.g., hexane, benzene, toluene), an ether (e.g., diethyl ether, dibutyl ether, tetrahydrofuran, dioxane) and in some cases a nitrile (e.g., acetonitrile, benzonitrile), a ketone (e.g., acetone, acetophenone) or a halocarbon (e.g., chloroform, carbon tetrachloride, chlorobenzene). When a reaction medium is used, the reactants may be either dissolved or suspended in the medium.

The reaction of this invention may be carried out over a temperature range from −80°C to about +80°C, and preferably in the range from 20°–50°C. The reaction is also a reversible type of equilibrium. It must therefore be recognized that in the upper temperature range, for example from 50° to 80°C, some of the carbon dioxide complexes of the invention, particularly those containing iridium, form in large yield whereas others form mostly in lower yields and a few selected complexes do not appear to form in measurable amounts. At temperatures substantially above 80°C, the complexes of this invention tend to lose carbon dioxide.

The pressure at which the reactions of this invention is carried out may be varied widely from below atmospheric pressure to above atmospheric pressure. Thus carbon dioxide pressures from as low as −12 psig up to 830 psig and above may be used. Preferred pressures are in the range of 5 to 600 psig, particularly at room temperature. Mixtures of carbon dioxide with other gases inert to the reactants and products may be used.

The time required for reaction of compounds of formula II with carbon dioxide varies widely, e.g., from 2–5 seconds to 3 days and more, depending on the compound involved.

The process of this invention has utility as a means for absorbing carbon dioxide and the products of the invention represent solid sources from which carbon dioxide can be recovered by the action of heat, reduced pressure or selected solvents. Thus a system for alternate absorption and regeneration of carbon dioxide is readily constructed as illustrated in Example 8.

The products of formula I are also useful as catalysts for hydrogenation and isomerization of olefins. This utility is illustrated in Example A.

In the disclosures which follow, parts are by weight unless otherwise indicated and temperatures are in degrees centigrade.

In the preparations of starting materials shown below at (a) to (f) and the examples which follow, all manipulations, unless otherwise noted, were performed under an argon atmosphere. The carbon dioxide used was Matheson Coleman Instrument Grade, 99.99% min. Pressure reactions were conducted in Pyrex glass pressure bottles.

The following abbreviations/codes are used:

dmpe = $(CH_3)_2PCH_2CH_2P(CH_3)_2$
depe = $(CH_3CH_2)_2PCH_2CH_2P(CH_2CH_3)_2$
dippe = $[(CH_3)_2CH]_2PCH_2CH_2P[CH(CH_3)_2]_2$
triars = $CH_3As[CH_2CH_2CH_2As(CH_3)_2]_2$
Me = $CH_3$
Et = $CH_2CH_3$ In the examples, the names of the products are given in the captions, abbreviations generally being used in the body.

a. $[Rh(dmpe)_2]^+Cl^-$ 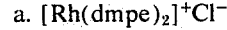

To a stirred, filtered solution of 2.0 g of Rh$_2$Cl$_2$(C$_2$H$_4$)$_4$ (Cramer, Inorg. Chem., 1, 722, 1962) in 100 ml of tetrahydrofuran was added dropwise a solution of 3.1 g of dmpe in 10 ml of tetrahydrofuran. The solution was kept for 16 hr. at ambient temperature followed by filtration and washing with ether to obtain a yellow solid. This was twice recrystallized from acetonitrile with toluene then dried to <0.1 micron affording the title compound in the form of a dark golden crystalline solid, m.p. >270°(dec).

Anal. Calcd. for C$_{12}$H$_{32}$P$_4$ClRh: C, 32.86; H, 7.35: Found: C, 32.27; H, 7.26. The compound's proton decoupled $^{31}$P nmr spectrum in acetonitrile-d$_3$ showed a doublet centered at −34.2 ppm, J(P—Rh) = 124 Hz.

b. [Rh(dmpe)$_2$]$^+$PF$_6^-$

To a stirred, filtered solution of Rh$_2$Cl$_2$(C$_2$H$_4$)$_4$ (3.0 g) in 120 ml of tetrahydrofuran was added AgPF$_6$ (3.9 g) in 30 ml of tetrahydrofuran. After filtration to remove the resulting grey solid, ¼ of the above solution was treated with dmpe (1.15 g) in 10 ml of tetrahydrofuran. Filtration followed by an ether wash afforded 1.85 g of yellow solid. 1.19 g of this was recrystallized from 150 ml of tetrahydrofuran with 20 ml of ether and dried to <0.1 micron yielding 0.66 g of the title compound in the form of yellow crystalline plates.

Anal. Calcd. for C$_{12}$H$_{32}$F$_6$P$_5$Rh: C, 26.29; H, 5.88; P, 28.26. Found: C, 26.07; H, 5.90; P, 28.52. The proton decoupled $^{31}$P nmr spectrum in acetonitrile-d$_3$ showed a doublet centered at −34.8 ppm, J(P—Rh) = 122 Hz.

c. [Ir(dmpe)$_2$]$^+$Cl$^-$

To a stirred solution of 3.25 g of Ir$_2$Cl$_2$(C$_8$H$_{14}$)$_4$ (Herde et al., Inorg. Syn. XV, 19, 1974) in 100 ml of benzene was added dropwise dmpe (2.18 g) in 10 ml of toluene. Stirring for 30 min. was followed by filtration and then benzene and pentane washes of the resultant solid. Drying to <0.1 mircon yielded the title compound in the form of a light orange solid (2.9 g), m.p. 252°–253°(dec).

Anal. Calcd. for C$_{12}$H$_{32}$P$_4$ClIr: C, 27.30; H, 6.10; P, 23.46; Cl, 6.72; Ir, 36.41. Found: C, 26.93; H, 5.99; P, 23.23; Cl, 6.48; Ir, 36.11.

d. [Ir(depe)$_2$]$^+$Cl$^-$

To a stirred solution of Ir$_2$Cl$_2$(C$_8$H$_{14}$)$_4$ (2.44 g) in 100 ml of benzene at ambient temperature was added dropwise depe (2.0 g) in 10 ml of benzene. After 3 hr the mixture was filtered. Recrystallization of the resultant solid from acetonitrile/ether followed by drying to <0.1 micron afforeded the title compound in the form of light red crystals (1.83 g), m.p. >190°(dec).

Anal. Calcd. for C$_{20}$H$_{48}$P$_4$ClIr: C, 37.52; H, 7.56; P, 19.35. Found: C, 37,03; H, 7.50; P, 19.11.

$^1$H, $^{31}$P, and $^{13}$C nmr spectra are consistent with the formulation [Ir(depe)$_2$]$^+$Cl$^-$.

e. [Ir(dippe)$_2$]$^+$Cl$^-$

To a stirred solution of Ir$_2$Cl$_2$(C$_8$H$_{14}$)$_4$ (3.26 g) in 150 ml of benzene was added to 3.36 g of dippe. After 3 hr the mixture was filtered and the resultant red solid washed with benzene and hexane. Recrystallization from acetonitrile with ether and then drying to <0.1 micron yielded the title compound in the form of red crystals (1.98 g), m.p. >280°.

Anal. Calcd. for C$_{28}$H$_{64}$P$_4$ClIr: C, 44.70; H, 8.58; P, 16.47. Found: C, 44.66; H, 8.59; P, 16.86. The pmr spectrum is consistent with the formulation [Ir(dippe)$_2$]$^+$Cl$^-$.

f. [Ir(PMe$_3$)$_4$]$^+$Cl$^-$

To a stirred solution of Ir$_2$Cl$_2$(C$_8$H$_{14}$)$_4$ (2.0 g) in 150 ml of toluene at 20°C was added PMe$_3$ (1.40 g) in 10 ml of toluene. After 3 days at −30° the mixture was filtered and the resultant solid washed with hexane. Drying to <0.1 micron afforded the title compound in the form of a dark orange solid (2.0 g).

Anal. Calcd. for C$_{12}$H$_{36}$P$_4$ClIr: C, 27.09; H, 6.82. Found: C, 27.45; H, 6.70.

EXAMPLE 1

(Carbon Dioxide)Tris(Triethylphosphine)Nickel

When 3.2 g of yellow Ni(PEt$_3$)$_4$ (Tolman et al., J. Organometal. Chem., 65, C23–C26, 1974) was dissolved in 10 ml of toluene, the solution turned deep violet in color with the formation of Ni(PEt$_3$)$_3$ by dissociation of ligand. This solution was pressured to 15 psig with CO$_2$ at 65° for 18 hours. The dark brown solution obtained showed new infrared bands at 1620 and 1670 cm$^{-1}$, indicating the presence of Ni(PEt$_3$)$_3$(CO$_2$).

EXAMPLE 2

(Carbon Dioxide)Tris(Triethylphosphine)Nickel 5.1 g of Ni[PEt$_3$]$_4$ was converted to Ni]PEt$_3$]$_3$ by heating to 55° under high vacuum. The resultant dark purple mass was extracted with 50 ml of hexane affording a dark purple solution. This was placed under 15 psig CO$_2$ at 55° for 2 days, yielding no pronounced color change. Removal of solvent under vacuum yielded a dark solid with no new i.r. spectral features. Redissolution in hexane followed by sparging with CO$_2$ at 55° until all solvent was removed resulted in a dark, purple-black solid exhibiting a new, weak i.r. band at 1650 cm$^{-1}$, showing the product to contain Ni(PEt$_3$)$_3$.(CO$_2$).

EXAMPLE 3

(Carbon Dioxide)Tris(Triethylphosphine)Platinum

A solution of 0.2 g of Pt(PEt$_3$)$_4$ (Guggenberger et al., J. Amer. Chem. Soc., 94, 5665–73, 1972) in 30 ml of hexane was sparged with CO$_2$ at ambient temperature until the solvent was evaporated. The infrared spectrum of the resulting pale yellow oil showed strong new bands at 1740 (sh), 1670 and 1630 cm$^{-1}$, showing the product to contain Pt(PEt$_3$)$_3$(CO$_2$).

When Pd(PEt$_3$)$_4$ (W. Kuran et al., Inorg. Chim. Acta, 12 (1975) 187–193) is substituted for Pt(PEt$_3$)$_4$ in the procedure of Example 3, the complex Pd(PEt$_3$)$_3$(CO$_2$), (carbon dioxide)tris(triethylphosphine)palladium, is obtained.

EXAMPLE 4

[Bis[3-(Dimethylarsino)Propyl]Methylarsine-As,As',As"]-(Carbon Dioxide)Chlorohodium]

A benzene solution of Rh(triars)Cl was placed under 23 psig CO$_2$. After 16 hr at 55° the solution was filtered and stripped, in vacuo, affording an orange solid with the i.r. spectral features of Rh(triars)Cl and new bands at 1660(m), 1620(s), and 1210(w) cm $^{-1}$, showing the product to contain Rh(triars)(CO$_2$)Cl.

EXAMPLe 5

(Carbon Dioxide)Bis[1,2-Ethanediylbis[Dimethylphosphine]-P,P']Rhodium(1+), Chloride A suspension of 0.5 g of [Rh(dmpe)$_2$]$^+$Cl$^-$ in 30 ml of benzene was pressured with 15 psig CO$_2$. After 2 days at 60° the mixture was filtered, yielding a yellow solid with new i.r. bands at 1630(m), 1600(w), and 1220(m) cm$^{-1}$, showing the product to contain Rh(dmpe)$_2$(CO$_2$)Cl.

EXAMPLE 6

(Carbon Dioxide)Bis[1,2-Ethanediylbis[Dimethylphosphine]-P,P']Rhodium(1+), Hexafluorophosphate(1−)

A solution of [Rh(dmpe)$_2$]$^+$PF$_6^-$ in 50 ml of tetrahydrofuran was pressured to 15 psig Co$_2$. After 18 hr at 62°, solvent removal, in vacuo, resulted in a yellow solid displaying a new i.r. band at 1620(w) cm$^{-1}$, showing the product to contain Rh(dmpe)$_2$(CO$_2$)PF$_6$.

EXAMPLE 7

(Carbon Dioxide)Bis[1,2-Ethanediylbis[Dimethylphosphine]-P,P']Iridium(1+), Chloride A suspension of the orange [Ir(dmpe)$_2$]$^+$Cl$^-$ (1.0 g) in 20 ml of benzene was placed under 15 psig CO$_2$ resulting, within minutes, in a suspension of a light tan solid. Stirring was continued at 60° for 4 days, after which the solid was collected, washed with benzene and hexane then dried to <0.1 micron. The resultant off-white solid, Ir(dmpe)$_2$(CO$_2$)Cl, m.p. 196°–198°(-dec), was air-sensitive and exhibited the i.r. spectrum of [Ir(dmpe)$_2$]Cl with additional bands at 1630(w), 1550(s), 1220(s) and 760(s) cm$^{-1}$.

Anal. Calcd. for C$_{13}$H$_{32}$O$_2$P$_4$ClIr: C, 27.30; H, 5.64; O, 5.60; P, 21.66; Cl, 6.20; Ir, 33.60. Found: C, 27.65; H, 5.76; O, 5.42; P, 21.56; Cl, 6.44; Ir, 33.29.

Ir(dmpe)$_2$(CO$_2$)Cl prepared in a similar reaction lost the i.r. bands due to the coordinated CO$_2$ upon treatment with methylene chloride. The mass spectrally identified gas resulting from heating or treatment with HCl of Ir(dmpe)$_2$(CO$_2$)Cl was CO$_2$.

EXAMPLE 8

(Carbon Dioxide)Bis[1,2-Ethanediylbis[Diethylphosphine]-P,P']Iridium(1+), Chloride

[Ir(depe)$_2$]$^+$Cl$^-$ (0.2 g) in an 80 ml mixture of acetonitrile, toluene, and hexane afforded a light red solution with undissolved red solid. Placement under 15 psig CO$_2$ for 36 hr at 70° yielded a colorless solution. Concentration to 40 ml, in vacuo, at ~40° caused darkening to an orange-gold color. 5 ml of acetonitrile was added and the resulting solution was treated with 14 psig CO$_2$ resulting, within minutes, in a colorless solution. Heating of the resultant bleached solution at 70°, in vacuo, caused reversion within minutes to an orange solution. The above CO$_2$ addition and evacuation cycle was repeated three times. The infrared spectrum of the colorless product from [Ir(depe)$_2$]$^+$Cl$^-$ and CO$_2$ showed it to contain Ir(depe)$_2$CO$_2$Cl.

EXAMPLE 9

(Carbon Dioxide)Bis[1,2-Ethanediylbis[Diethylphosphine]-P,P']Iridium(1+), Hexafluorophosphate(1−)

A 20 ml acetonitrile solution of [Ir(depe)$_2$]$^+$Cl$^-$ (0.2 g) was treated with AgPF$_6$ (0.08 g) in 20 ml of acetonitrile. After 10 the mixuture was filtered and extracted with acetonitrile affording a dark orange solution. The red oil resulting from solvent removal from a portion of the above solution exhibited an i.r. spectrum consistent with the formulation [Ir(depe)$_2$]$^+$PF$_6^-$. A third of the above solution was subjected to 15 psig CO$_2$ resulting, within minutes, in a light tan solution. Evacuation at 72° yielded a dark orange solution, and subjection of this to 15 psig CO$_2$ again resulted in a bleached, off-white solution containing Ir(depe)$_2$(CO$_2$)PF$_6$.

EXAMPLE 10

(Carbon Dioxide)Bis[1,2-Ethanediylbis[Bis(1-Methylethyl)-Phosphine]-P,P°]Iridium(1+), Chloride A light red solution of [Ir(dippe)$_2$]$^+$CL$^-$ (0.1 g) in 20 ml of acetonitrile was pressured to 15 psig CO$_2$ for 60 hr at 67°. Solvent removal, in vacuo, afforded a light red solid with new i.r. bands at 1660(m) and 1620(w) cm$^{-1}$, indicative of Ir(dippe)$_2$(CO$_2$)Cl.

EXAMPLE 11

(Carbon Dioxide)Tetrakis(Trimethylphosphine)Iridium(1+), Chloride

The dark orange [Ir(PMe$_3$)$_4$]$^+$CL$^-$ (0.3 g) was crushed to fine particles and then suspended in 20 ml of benzene. The system was pressured to 10 psig CO$_2$ and then stirred at ambient temperature for 18 hr, then at 71° for 3 days, resulting in a light yellow suspension. Filtration followed by benzene and hexane washes afforded a light tan solid with new i.r. bands at 1700–1600(vs), 1230(w), 1210(w), 835(w), and 825(w) cm$^{-1}$ showing the product to contain Ir(PMe$_3$)$_4$(CO$_2$)CL.

EXAMPLE 12

Bis(Carbon Dioxide)Chlorotris(Trimethylphosphine)Iridium

To a stirred solution of Ir$_2$Cl$_2$(C$_8$H$_{14}$)$_4$ (1.0 g) in 60 ml of benzene was added PMe$_3$ (0.68 g). After 2 days the solution was stripped to dryness and the residue recrystallized from toluene with hexane, affording dark yellow crystals (0.70 g). One-half of this product in 15 ml of benzene was pressured to 10 psig CO$_2$. Filtration after 24 hr yielded white crystals (0.21 g), with new i.r. bands at 1600–1750(s) cm$^{-1}$. X-ray crystal structure determination showed the product to be IrCl[(CO$_2$)$_2$](PMe$_3$)$_3$.

EXAMPLE 13

Bis(Carbon Dioxide)Chloro[Bis[3-(Dimethylarsino)propyl]-Methylarsine-As, As', As"]Iridium To 1.0 g of Ir$_2$Cl$_2$(C$_8$H$_{14}$)$_4$ in 80 ml of benzene was added to dropwise 0.91 g of triars. The resulting cloudy, dark yellow solution was decanted from some brown gum and treated with 100 ml of hexane. Filtration and extraction with benzene afforded a yellow solution which on concentration to dryness yielded a dark yellow solid. This solid was dissolved in 50 ml benzene and the solution pressured to 16 psig CO$_2$. The system was then evacuated and repressured with CO$_2$ and held for 3 days at 70°C. Filtration gave a yellow solid which was extracted with benzene and dried under vacuum <0.1 micron.

Anal. Calcd. for C$_{13}$H$_{27}$O$_4$ClAs$_3$Ir: C, 23.73; H, 3.82; O, 8.98. Found: C, 23,36; H, 4.39 O, 8.20.

The infrared spectrum showed new bands at 1720–1600(S), 990 (m) and 780 (m) cm$^{-1}$, indicating the product to be IrCl[(CO$_2$)$_2$](triars).

The $CO_2$ complexes of formula I are useful as catalysts for isomerization and hydrogenation of olefins. This is illustrated in the following:

EXAMPLE A

A suspension of 0.06 g of $Ir(dmpe)_2(CO_2)Cl$ (Example 7) in 10 ml of benzene was evacuated, pressured to 0 psig with 1-butene, to 30 psig with hydrogen and then to 35 psig with $CO_2$. The bottle was agitated and the temperature increased from 25°C to 90°C over a 6 hour period. Gas samples were taken periodically for chromatographic analysis. Formation of 2-butene was observed at 30°–60°C and butane formation was evident at 90°C. This shows that the complex catalyzed the isomerization and hydrogenation of 1-butene, since in a control experiment without $Ir(dmpe)_2(CO_2)Cl$ neither 2-butene nor butane was found.

We claim:

1. A carbon dioxide/metal complex of the formula $ML_m(CO_2)_nX_p$, wherein:

M is Rh, Ir, Ni, Pd, or Pt;
L is one equivalent of an acyclic tertiary alkyl phosphine or arsine ligand in which each alkyl group is saturated and may contain up to 18 carbons;
X is one equivalent of an anion; and
when M is Rh or Ir
  $m$ is 3 to 4
  $n$ is 1 or 2
  $p$ is 1, and
  $m + n$ does not exceed 5;
when M is Ni, Pd or Pt
  $m$ is 3,
  $n$ is 1, and
  $p$ is 0.

2. A compound of claim 1, (carbon dioxide)tris-(triethylphosphine)nickel.

3. A compound of claim 1, (carbon dioxide) tris-(triethylphosphine)platinum.

4. A compound of claim 1, [bis[3-(dimethylarsino)propyl]methylarsine-As,As',As''](carbon dioxide)-chlororhodium.

5. A compound of claim 1, (carbon dioxide)bis-[1,2-ethanediylbis[dimethylphosphine]-P,P']rhodium(1+), chloride.

6. A compound of claim 1, (carbon dioxide)bis[1,2-ethanediylbis[dimethylphosphine]-P,P']rhodium(1+), hexafluorophosphate(1−).

7. A compound of claim 1, (carbon dioxide)bis [1,2-ethanediylbis[dimethylphosphine]-P,P']iridium(1+), chloride.

8. A compound of claim 1, (carbon dioxide) bis ]1,2-ethanediylbis[diethylphosphine]-P,P']iridium (1+), chloride.

9. A compound of claim 1, (carbon dioxide)bis[1,2-ethanediylbis[diethylphosphine]-P,P']iridium(1+), hexafluorophosphate(1−).

10. A compound of claim 1, (carbon dioxide)bis[1,2-ethanediylbis[bis(1-methylethyl)phosphine]-P,P']iridium(1+), chloride 11. A compound of claim 1, (carbon dioxide)tetrakis(trimethylphosphine)iridium(1+), chloride.

12. A compound of claim 1, bis(carbon dioxide)-chlorotris(trimethylphosphine)iridium.

13. A compound of claim 1, bis(carbon dioxide)chloro[bis[3(dimethylarsino)propyl]methylarsine-As,As,',As'']-iridium.

14. The process of preparing a compound of claim 1 which comprises reacting $n$ moles of carbon dioxide with a complex of the formula $ML_mX_p$ wherein M, L, X, $m$, $n$, and $p$ are as defined in claim 1.

15. The process of claim 14 wherein the complex is $Ni[P(C_2H_5)_3]_3$.

16. The process of claim 14 wherein the complex is $(Ir[(CH_3)_2PCH_2CH_2P(CH_3)_2]_2)^+Cl^-$.

* * * * *

UNITED STATES PATENT OFFICE
CERTIFICATE OF CORRECTION

PATENT NO. : 3,954,821
DATED : May 17, 1976
INVENTOR(S) : Thomas Herskovitz and George William Parshall It is certified that error appears in the above-identified patent and that said Letters Patent are hereby corrected as shown below:

Column 7, line 29 in claim 1 the word "to" should read --or--.

Column 8, line 6 in claim 5 the "-" after the word bis should be deleted.

Signed and Sealed this

Thirteenth Day of July 1976

[SEAL]

Attest:

RUTH C. MASON
Attesting Officer

C. MARSHALL DANN
Commissioner of Patents and Trademarks